(12) United States Patent
Nordheim et al.

(10) Patent No.: US 6,193,753 B1
(45) Date of Patent: Feb. 27, 2001

(54) EXTERNAL PENILE PROSTHESIS

(76) Inventors: James D. Nordheim; Cathleen Nordheim, both of 1174 Jedidah Way, Round O, SC (US) 29474

( * ) Notice: Subject to any disclaimer, the term of this patent is extended or adjusted under 35 U.S.C. 154(b) by 0 days.

(21) Appl. No.: 09/257,620

(22) Filed: Feb. 25, 1999

Related U.S. Application Data (60) Provisional application No. 60/076,047, filed on Feb. 26, 1998.

(51) Int. Cl.$^7$ .................................. A61F 2/02; A61F 5/00
(52) U.S. Cl. .......................................... 623/11.11; 600/38
(58) Field of Search ........................... 623/11.11; 600/38, 600/39, 40

(56) References Cited

U.S. PATENT DOCUMENTS

| | | | |
|---|---|---|---|
| 2,378,795 | * 6/1945 | Rupe | 600/39 |
| 3,495,589 | 2/1970 | Clement . | |
| 3,820,533 | 6/1974 | Jones | 128/79 |
| 3,939,827 | 2/1976 | Brunstetter | 128/79 |
| 4,224,933 | 9/1980 | Reiling | 128/79 |
| 4,281,648 | 8/1981 | Rogers | 128/79 |
| 4,407,275 | * 10/1983 | Schroeder | 128/79 |
| 4,432,357 | 2/1984 | Pomeranz | 128/79 |
| 4,523,584 | * 6/1985 | Yachia et al. | 128/79 |
| 4,564,006 | 1/1986 | Pomeranz | 128/79 |
| 4,899,737 | 2/1990 | Lazarian | 128/87 A |
| 4,960,113 | 10/1990 | Seeberg-Elverfeldt | 128/79 |
| 5,370,601 | 12/1994 | Collins | 600/41 |
| 5,445,594 | * 8/1995 | Elist | 600/38 |
| 5,509,891 | 4/1996 | DeRidder | 600/39 |
| 5,522,787 | 6/1996 | Evans | 600/39 |
| 5,823,939 | 10/1998 | Tsagarakis | 600/38 |

* cited by examiner

*Primary Examiner*—Vincent Millin
*Assistant Examiner*—Alvin Stewart

(74) *Attorney, Agent, or Firm*—Jerry Johnson (57) ABSTRACT

An external penile prosthesis comprises a support including an expandible bladder having at least first and second elastic layers. The first and second layers are secured together to include an interior expandible bladder chamber between the first and second surfaces. The support is secured into a tube shape. The length of the support is substantially equal to the length of a male penis from the base to the coronal ridge of the glans. The tube is selectively dimensioned for a snug but not tight fit on the penis which does not cause restriction of blood flow through the veins beneath the skin of the penis. The prosthesis includes a valve for insertion of a fluid into the expandible bladder chamber of the support. The expandible bladder chamber of the support may be selectively filled with fluid from a first non-expanded condition where the support has little rigidity and the support does not substantially add to the circumference of the penis, to a second fully expanded condition where the support has high supportive rigidity and adds substantially to the circumference of the penis. The external penile prosthesis further includes the use of a thickened bladder layer or properly located additional rigid stays to minimize localized constriction of the inside diameter as the expandible bladder expands. Upon insertion of a fluid into the interior expandible bladder chamber, the means to minimize localized constriction of the inside diameter cause the outside diameter of the tube to expand a greater amount than the interior of the tube constricts. The use of a thickened layer in addition to rigid stays is also possible. The support may comprise a generally planar panel having a width of predetermined size to approximate the circumference of the penis for wrapping the support around the penis. A condom applied on top of the support may be used to secure the support in a tube shape. Additionally, a tab of material attached to the generally planar panel for wrapping around the penis, to aid in the retention of the support in the wrapped condition, may also be used. The tab may include a length substantially equal to the length of the planar support, such that the tab comprises a cover for the support. A condom may also be used in addition to the use of the tab.

18 Claims, 8 Drawing Sheets

EXTERNAL PENILE PROSTHESIS

RELATED APPLICATIONS

The present application claims the benefit under Title 35, United States Code, Section 119E of the U.S. Provisional Patent Application serial No. 60/076,047, filed Feb. 26, 1998 entitled "Inti-mate (Inflatable Penile Support Sleeve)".

BACKGROUND

Existing penile prostheses include a first type which includes a device to manipulate blood flow within the penis. The most common device to manipulate blood flow within the penis is a ring or sleeve that applies constrictive pressure to the base of the penis to reduce blood flow through the veins which are located just beneath the skin of the penis. These rings or sleeves permit blood flow to enter the penis through the arteries of the penis, but restrict the flow of blood out of the penis. The accumulation of blood through the use of these devices results in many cases in an erection in the penis.

Prosthetic devices of this type have used various structures to apply a constrictive pressure on the penis, typically at the base of the penis proximate to the body. Some of the devices use sleeves which may be inflated with a pressurized fluid (typically air). Upon inflation, the sleeve expands inwardly to apply a constrictive pressure on the base of the penis. Many of these designs use inflatable bladders having inner and outer layers which are of unequal thicknesses and therefor unequal expansion rates. Specifically, these prostheses have thicker layers of material on the outside of the bladder than the inside of the bladder to encourage inward expansion of the bladder. Other prosthetic devices of this type have used a rigid body outside the inflatable bladder to ensure that inflation will provide inward expansion with the subsequent constriction of the penis.

This type of penile prostheses is commonly used when a decrease in blood flow within the penis occurs. Men who suffer from diabetes would be an example of those who would benefit from this type of prostheses.

For patients that have insufficient blood flow in the penis to create an accumulation of blood in the penis and create an erection in the penis, prostheses of this type are of little use.

A detrimental aspect of constricting prostheses of this type is the tissue damage that could be incurred if the prosthesis is left in place for an extended period of time. Were a user of this type of prostheses to fall asleep while wearing the prosthesis, serious injury would probably result.

Other penile prostheses do not encourage constriction of the penis. Theses prostheses are used primarily to add rigidity to the penis so that the user can engage in intercourse. The prostheses of this type, when used with the penis, simulate an erection. These prostheses are suitable for use by those who may have a diminished blood flow and may not achieve an adequate erection to engage in intercourse, as well as those who may have disease damaged tissue that prohibits an erection from occurring.

A first example of a penile prostheses of this type is shown in U.S. Pat. No. 3,939,827. This penile prosthesis uses a rigid splint which is placed against the penis and retained on the penis by a cover of flexible material. The cover is non-rigid and does not support the penis. The rigid splint has a shape to conform to the cylindrical shape of the penis.

A second example of penile prostheses that do not encourage constriction of the penis is shown in U.S. Pat. No. 5,522,787. This penile prosthesis uses a non-rigid support that is constructed of soft, elastic, resilient material such as cellular polyurethane which is cut into a panel to be wrapped around the penis. A semi-rigid stiffener may be used with the non-rigid support to enhance the resistance to bending of the prosthesis.

Both of the first and second examples of non-constricting prostheses offer somewhat adjustable sizing as the support or support cover is wrapped around the penis.

Neither of these supports allow for the adjustment of the rigidity or circumferential size of the prosthesis after it is placed on the penis. Actually, adjustment to the rigidity of either of these prostheses would require the use of a different stiffener in either of the examples, or require a different material to be used in the non-rigid support of the second example.

There is a need for a penile prosthesis which is suitable for use by those who may have a diminished blood flow and may not achieve an adequate erection to engage in intercourse, as well as those who may have disease damaged tissue that prohibits an erection from occurring. There is a need for this penile prosthesis to allow for the adjustment of the rigidity and circumferential size of the prosthesis after it is placed on the penis. This adjustment allows the prosthesis to adjust to the extent that a user may achieve an erection, as well as to adjust to the desired physical properties of the prosthesis for the sexual enjoyment of those who would use the prosthesis.

SUMMARY

The present invention satisfies the previously mentioned needs for an external penile prosthesis.

The external penile prosthesis comprises a support including an expandible bladder having at least first and second elastic surfaces. The first and second surfaces are secured together to include an interior expandible bladder chamber between the first and second surfaces. The prosthesis includes means to secure the support into a tube shape with the first surface providing an inside surface of the tube and the second surface providing an outside surface of the tube. The support may be secured in a tube shape of predetermined size having an inside diameter, an outside diameter, and first and second ends defining a length. The length is substantially equal to the length of a male penis from the base to the coronal ridge of the glans. The second end of the support does not extend over the glans. The tube is selectively dimensioned for a snug but not tight fit on the penis which does not cause restriction of blood flow through the veins beneath the skin of the penis.

The external penile prosthesis includes a valve for insertion of a fluid into the expandible bladder chamber. The expandible support of the external penile prosthesis may be selectively filled with fluid from a first non-expanded condition where the support has little rigidity and the support does not substantially add to the circumference of the penis, to a second fully expanded condition where the support has high supportive rigidity and adds substantially to the circumference of the penis.

The external penile prosthesis further includes means to minimize localized constriction of the inside diameter as the expandible bladder expands. Upon insertion of a fluid into the interior expandible bladder chamber, the means to minimize localized constriction of the inside diameter cause the outside diameter of the tube to expand a greater amount than the interior of the tube constricts.

Localized constriction of the tube inside diameter may be minimized substantially along the entire length of the tube.

The means to minimize the constriction of the inside diameter as the expandable bladder expands comprises the first layer of the bladder having higher rigidity than the second layer of the bladder.

Alternatively, the means to minimize the constriction of the inside diameter as the expandable bladder expands comprises substantially rigid stays disposed on the first layer of the bladder for placement proximate to the penis. The rigid stays minimize the forces resulting from internal fluid pressure in the interior expandable bladder chamber from applying a localized pressure on the veins of the penis. The use of a thicker first layer in addition to rigid stays is also possible.

The support may comprise a generally planar panel having a width of predetermined size to approximate the circumference of the penis for wrapping the support around the penis. The panel includes opposite side edges which are disposed proximate to each other when the support is wrapped around the penis. The means to secure the support in a tube shape in this version may comprise a condom applied on top of the support. Alternatively, the means to secure the support in a tube shape in this version may comprise a tab of material attached to the generally planar panel for stretching across the first and second side edges to secure the side edges proximate to each other. The tab may include a width of predetermined size to approximate the circumference of the penis for wrapping the tab around the penis after the support has been wrapped around the penis for securing the support in the tube shape. Additionally, the tab may include a length substantially equal to the length of the planar support, such that the tab comprises a cover for the support. A condom may also be used in addition to the use of the tab.

The external penile prosthesis provides benefits that have been previously unavailable in penile prostheses.

By using a support that is wrapped around a penis, the prosthesis is adjustable in size and will accommodate most flaccid penises. Once the support of the prosthesis is wrapped around the penis, the support is adjustable in circumference and rigidity. This benefit is accomplished by the use of an inflatable expandable bladder. The prosthesis uses a an inflatable expandable bladder while providing a structure that minimizes constriction of the penis. Therefor, users of the prosthesis of the present invention will benefit from size and rigidity adjustments provided by the use of an inflatable expandable bladder. At the same time, the known risks associated with the manipulation of blood flow in the penis by using an inflatable prosthesis are greatly minimized.

The penile prosthesis of the present invention is easy to use. The inflatable support of the prosthesis may be quickly and easily wrapped around a penis. The support will remain retained on the penis while a condom is applied over the penis. The support may be quickly expanded to the desired rigidity and circumference through the inflation of the expandible bladder. The support will also conform to the shape of the penis, and will accommodate the use of rigid stays which provide enhanced rigidity of the support. After use, the prosthesis may be easily cleaned. Finally, the prosthesis includes no materials which will pose a threat to the health of those who would use the prosthesis. No adhesives, or other materials not typically used in medical applications are included in the construction of the prosthesis.

The prosthesis uses a support which may be wrapped around the penis to be snug, but which ensures blood flow though the penis will not be restricted by the application of a localized constrictive force applied by the support on the penis. The prosthesis, although possessing the rigidity in use to facilitate sexual intercourse, retains the flexibility to allow expansion of the penis without restricting blood flow in the veins and arteries of the penis. This allows for the accommodation of a partial or complete erection should an erection occur in the user.

The adjustment to the circumference and rigidity of the support and therefor the entire penis, is accomplished by insertion of a pressurized fluid (typically air) into an internal bladder expansion chamber. A simple pump bulb may be used for the insertion of pressurized fluid into the internal bladder expansion chamber through a simple valve on the bladder.

The prosthesis of the present invention provides an even thickness over the penis. Both the support and the retention tab are typically wrapped once around the penis. This results in no elevated ridges that may irritate the walls of a vagina. The support expand evenly around the penis and evenly in relation to the length of the penis.

The glans of the penis are not covered by the support of the prosthesis. This allows the many sensory nerve endings which aid in ejaculation of the penis, to be stimulated during intercourse while using the prosthesis. The exposure of the glans along with no interruption of blood flow through the penis, will allow many users to engage in sexual activities and to possibly experience an ejaculation, an erection, or both.

These and other advantages of the present invention will become apparent upon inspection of the accompanying specification, claims and drawings.

DESCRIPTION

Figure 1:
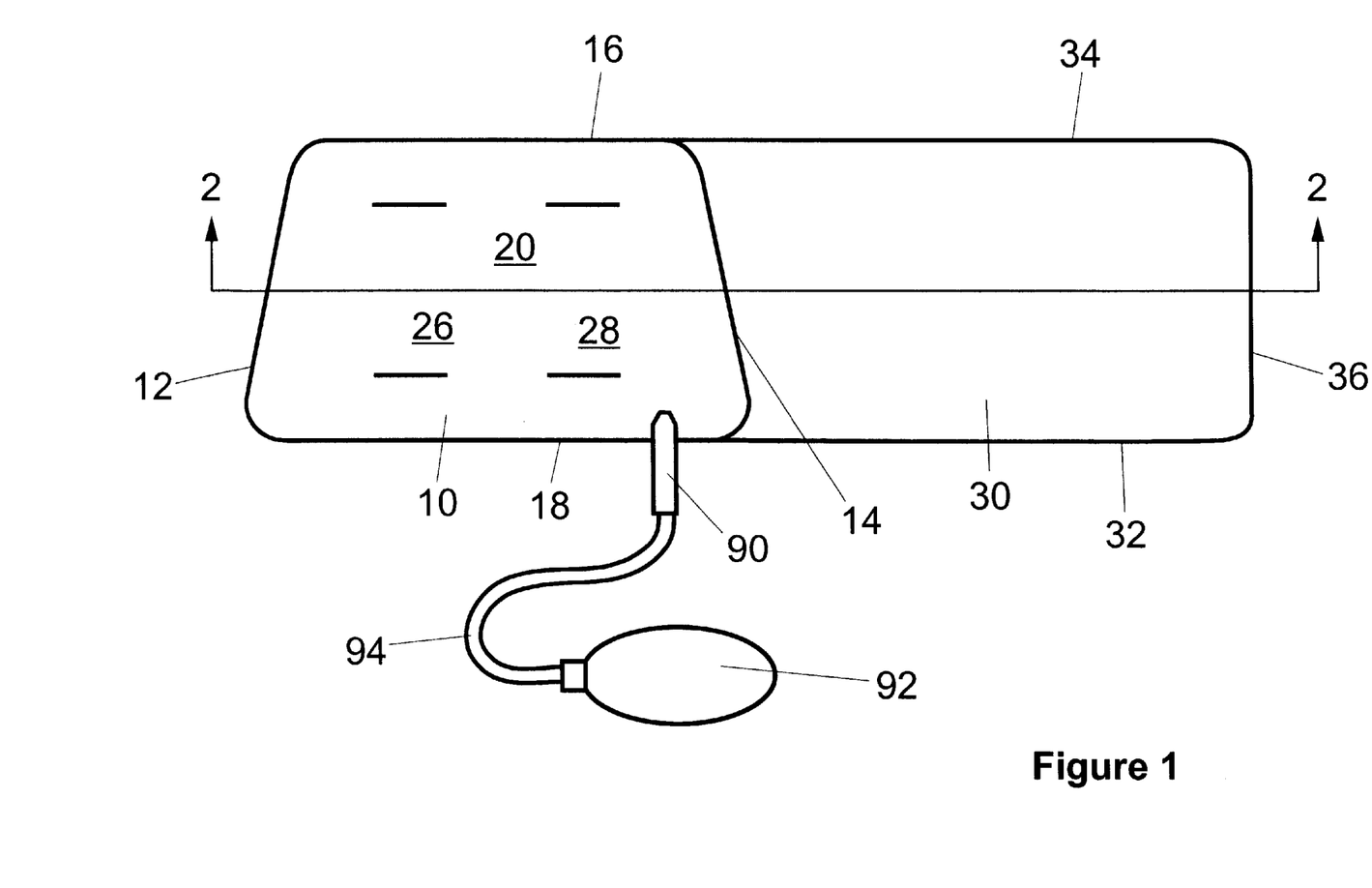
FIG. 1 is a top view of the prosthesis of the present invention

The external penile prosthesis of the present invention is shown in a top view in FIG. 1. The prosthesis includes a generally planar support 10. The support includes a first side edge 12 and a second side edge 14. The distance of the first side edge to the second side edge defines the width of the support. The width approximates the circumference of a flaccid penis so that the planar support can be wrapped into a tube around a penis. The support further includes a top edge 16 and a bottom edge 18. The distance from the top edge to the bottom edge defines the length of the support. The length approximates the length of a flaccid penis from the base where the penis is attached to the body to the coronal ridge of the glans. The support has a four sided shape approximating a trapezoid. This assists in the creation of a tube having a slight conical shape.

The first layer 20 of the support is shown in this figure, as well. Disposed on this layer are stay retaining panels 26 and 28. Stay retaining panels 26 and 28 are both attached on two sides to the first layer 20, but are separated at the top and bottom of the panels from the first layer 20. The separations are shown as top and bottom slits. The slits provide openings to insert a rigid stay (not shown) which is held against the first layer 20 beneath the retaining panels.

Attached to the side edge 14 is a tab 30 which serves to secure the support in a tube shape. The tab is a panel of similar length and width as the support. The tab 30 includes a top edge 34, a bottom edge 32, and a distal side edge 36. The tab 30 includes a length and width dimensioned to wrap around the penis and overlap the support once the support is wrapped around the penis. Accordingly, the tab will secure the support in a tube shape.

FIG. 1 further shows a valve 90, a pump ball 92, and a hose 94.

Figure 2:
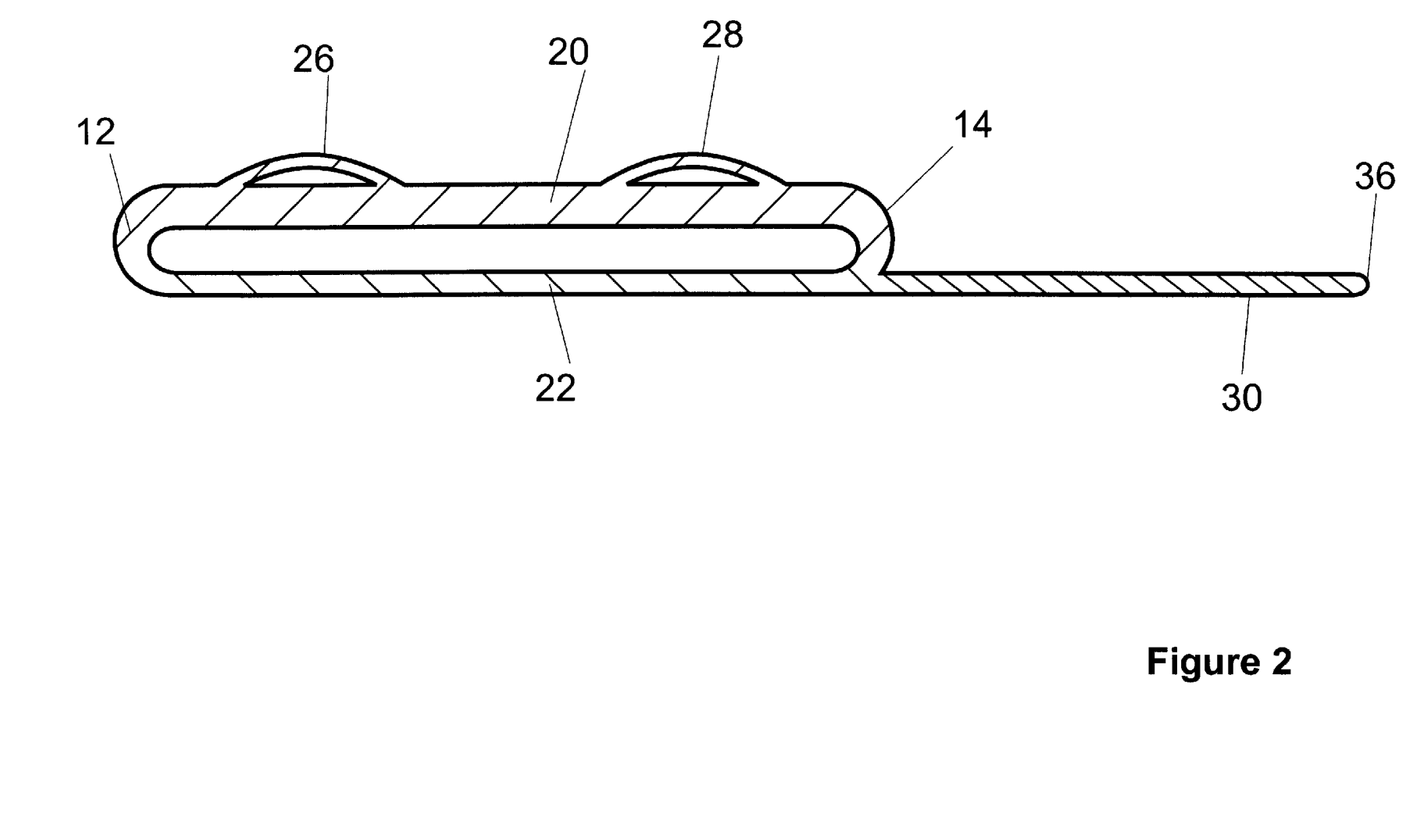
FIG. 2 is a cross-sectional side view of FIG. 1.

FIG. 2 shows a cross section of FIG. 1. This drawing shows that the support includes a first layer 20, and a second layer 22. The first and second layers are substantially of an identical size and are attached around their perimeter edges to create a bladder having an interior expandable bladder chamber disposed in the area separating the first and second layers. The first and second layers, as well as the tab 30, are all constructed of a medical grade plastic polymer such as 2706 Crayton manufactured by Caldwell Gasket. The medical grade plastic is elastic and is also tacky to the touch as it has limited self adhering properties.

The first layer 20 is shown thicker than the second layer 22. The tab 30 is shown to be constructed from a thinner layer of material than the first and second layers. Stay retaining panels 26 and 28 are also shown in cross-section in this view and are raised above the first layer 20.

Figure 3:
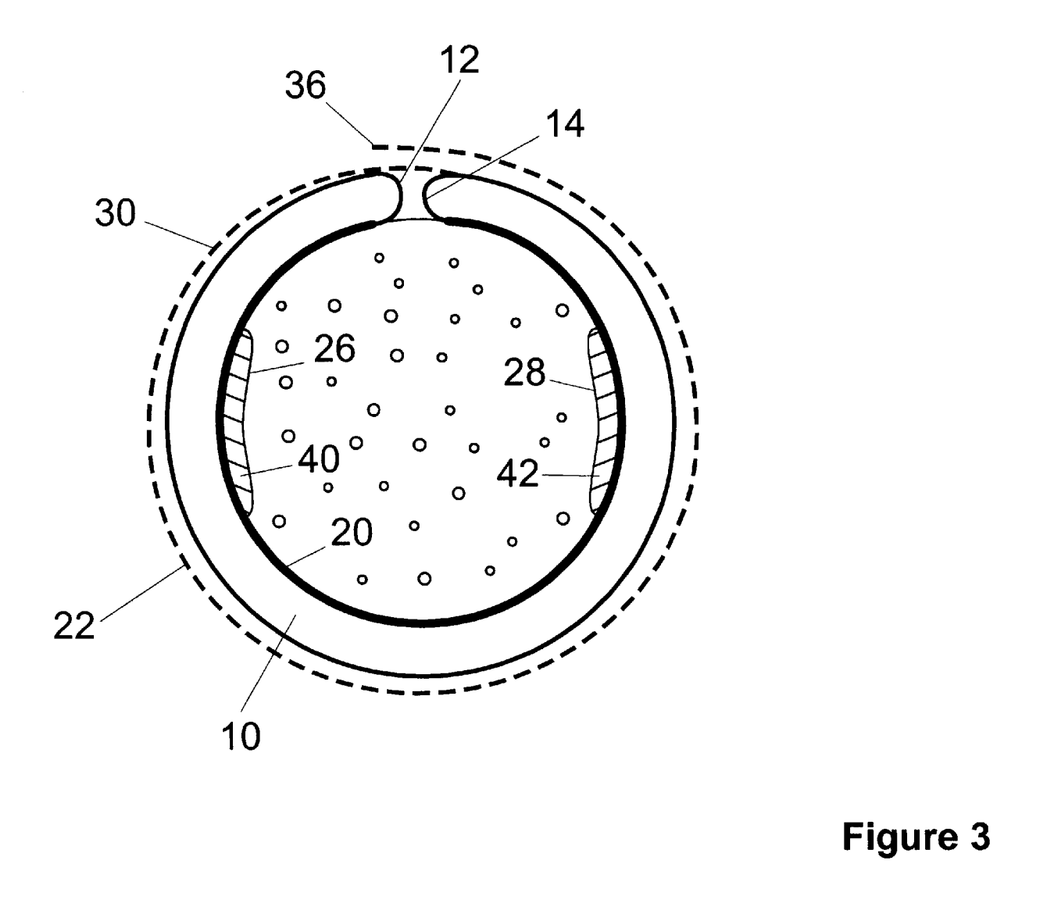
FIG. 3 is a cross-sectional view of a first version of the prosthesis wrapped around a penis.

FIG. 3 shows a cross-sectional view of the penile prosthesis of the present invention wrapped around a penis. The support 10 is shown in a tube shape wrapped around the shaft of the penis with the first side edge 12 proximate to the second side edge 14 at the top of the penis. The first layer 20 and second layer 22 of the expandable bladder of the support are shown separated by the air filled bladder chamber. Disposed around the support is tab 30 shown in dashed lines beginning proximate to the side edge 14 and making a full revolution around the circumference of the penis immediately on top of the tube shaped support.

Disposed within the stay retention panel 26 is a stay 40. Similarly, disposed within the stay retention panel 28 is a stay 42. The stays are shown having a concave shape to engage the sides of the penis. In this position, the stays are adjacent to the largest veins of the penis and serve to restrict any localized constrictive force that the expanded bladder would apply on the sides of the penis which might restrict circulation within the veins.

Additionally, the thickened first layer 20 of the support is disposed adjacent to the penis shaft. The thickened material minimizes any localized constriction of the penis as the thickened layer ensures that the outside diameter of the support will expand outwardly a greater amount that the interior diameter will constrict as the bladder is expanded during inflation. The thickened material of layer 20 minimizes constriction of the tube inside diameter from the base of the penis where the veins and arteries enter the penis, to the coronal ridge of the glans of the penis. Additionally, the layers of the support are manufactured to provide for substantially equal expansion of the support from the first to the second end of the support.

Figure 4:
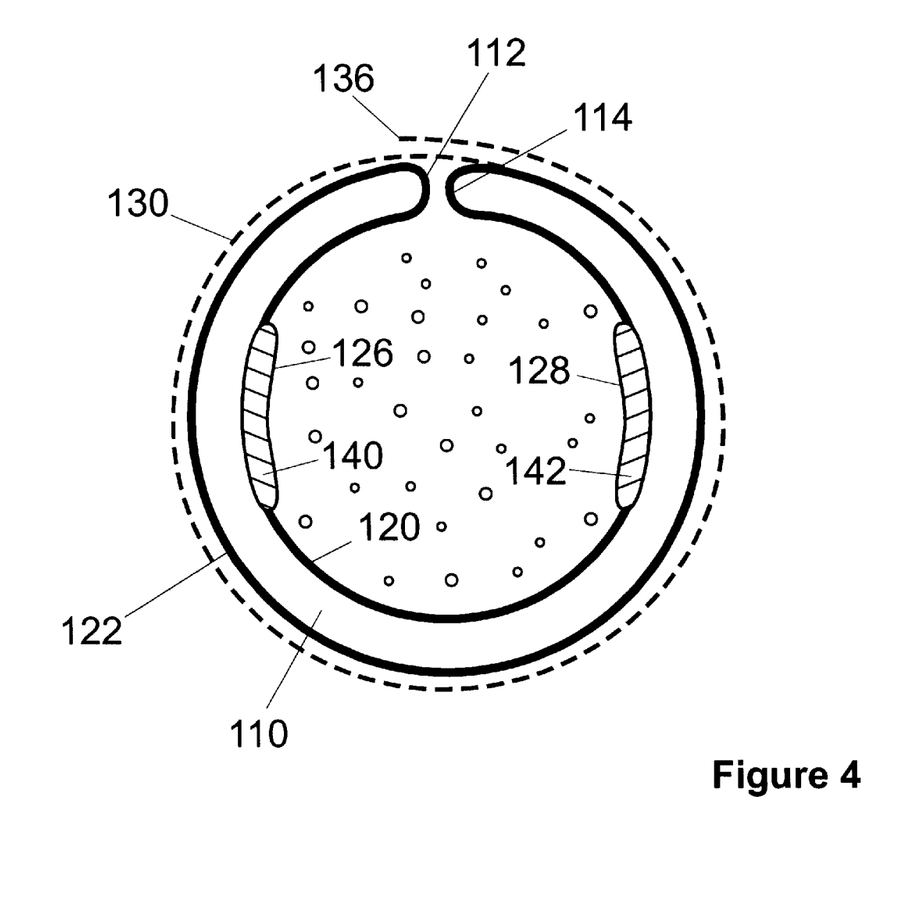
FIG. 4 is a cross-sectional view of a second version of the prosthesis wrapped around a penis.

FIG. 4 shows a second version of the invention. In this version, the means to minimize localized constriction of the support on the penis are the stays 140 and 142. The first layer 120 is not shown thicker than the second layer 122 in this version. The stays in this version may be of a length to extend substantially the entire length of the penis from the base to the coronal ridge of the glans.

Figure 5:
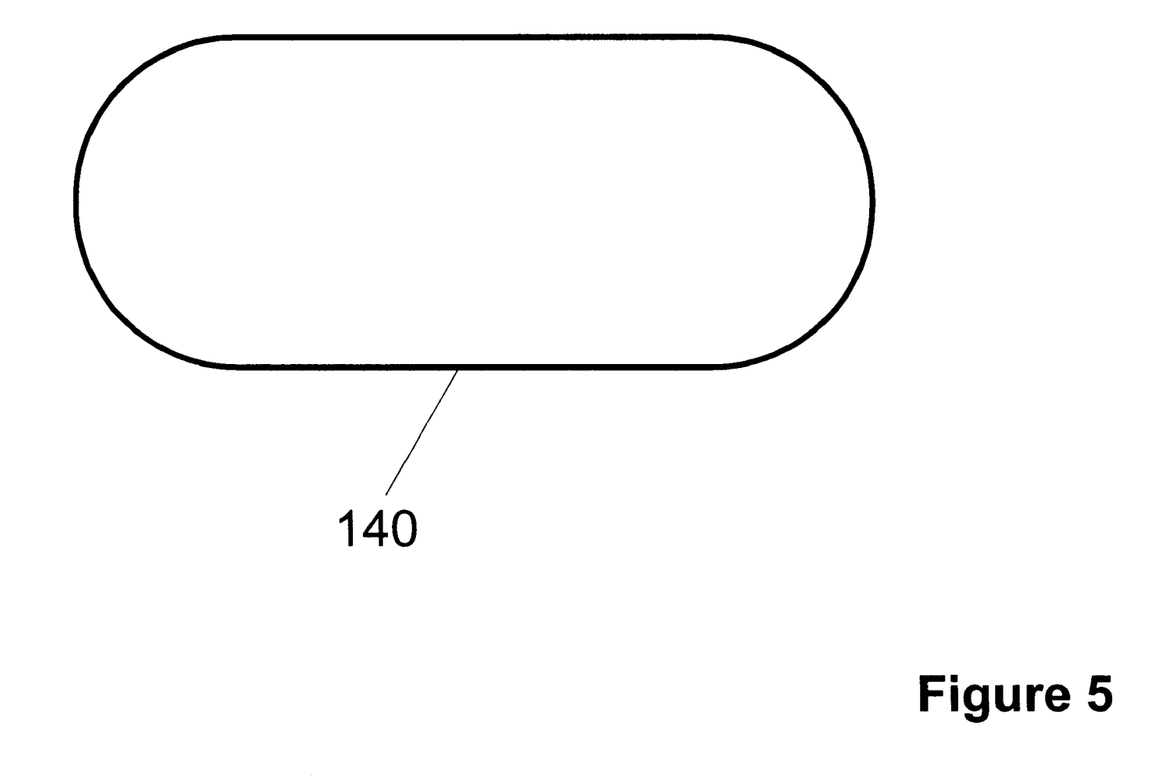
FIG. 5 is a top view of a rigid stay of the present invention.
Figure 6:
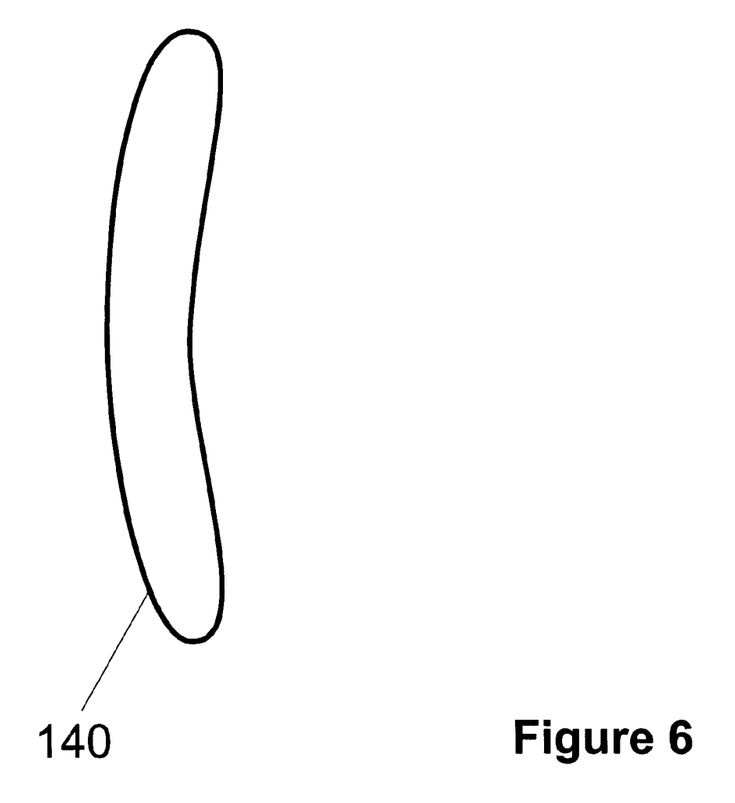
FIG. 6 is a side view of a rigid stay of the present invention.

FIGS. 5 and 6 show front and side views of a version of the stays 140. The stays typically comprise a convex plate manufactured from rigid plastic. The stays are usable along with the support only if it is desired to enhance the rigidity of the support. It is possible that only a single stay, or more than two stays could be used in the support. It is also possible that the stays could be positioned on the top and bottom of the penis, although this would decrease the protection from constriction that the stays provide to the veins on the sides of the penis.

Figure 7:
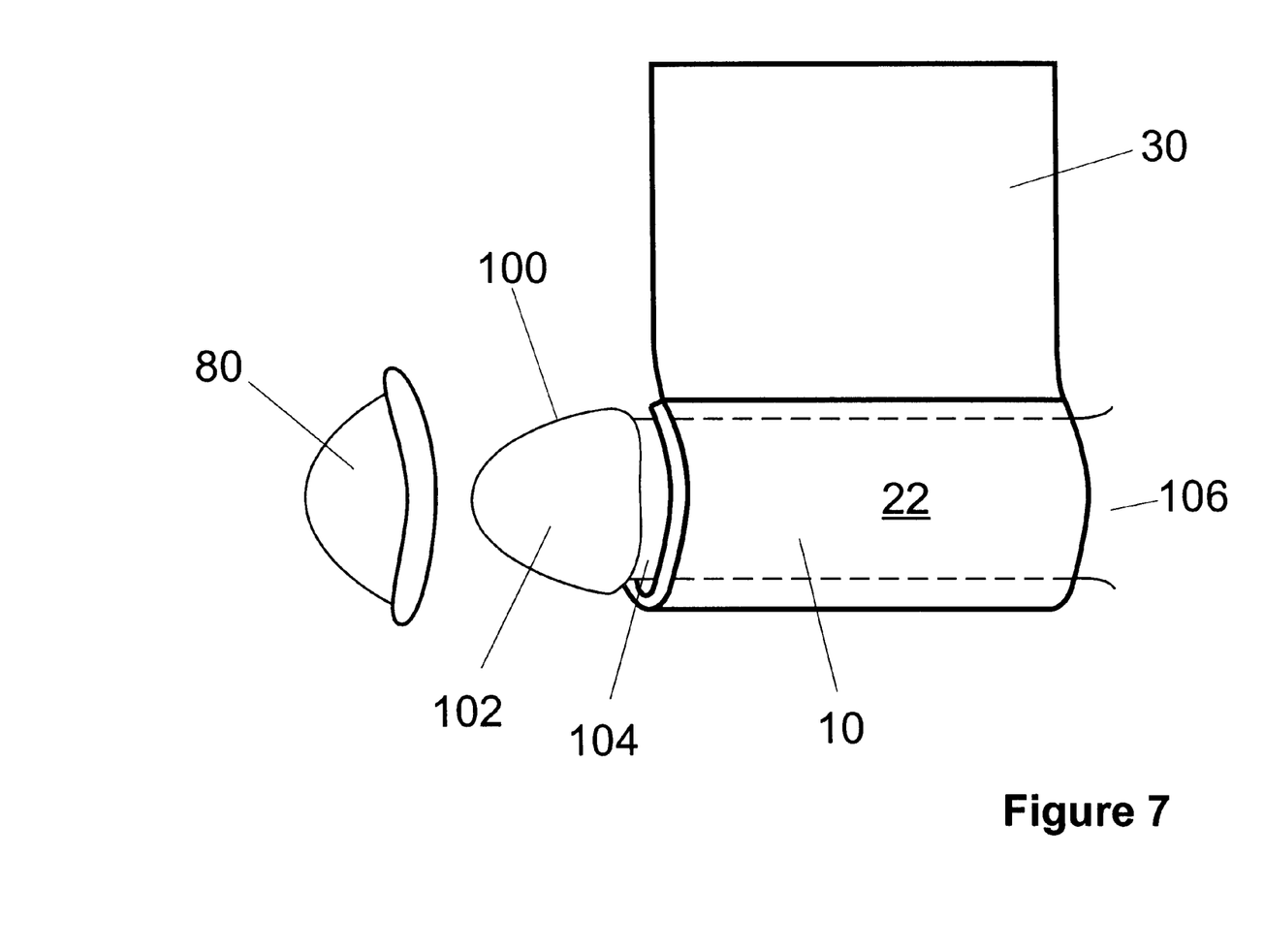
FIG. 7 is a side view of the prosthesis of the present invention wrapped around a penis.
Figure 8:
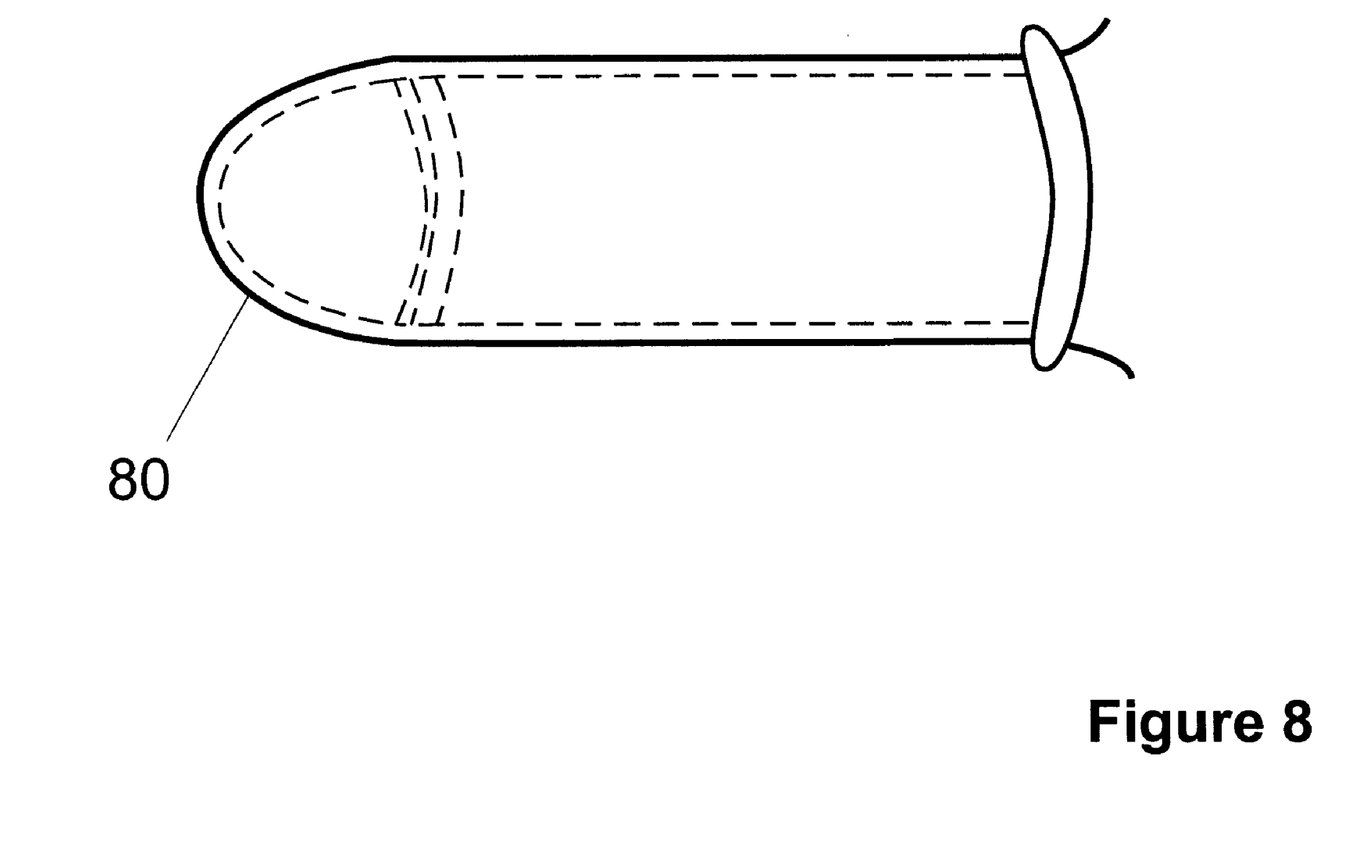
FIG. 8 is a side view of the prosthesis of the present invention wrapped around a penis and including a condom for use with the invention.

FIGS. 7 and 8 show the external penile prosthesis as it is used on a penis. FIG. 7 shows the support 10 in a tube shape wrapped around the flaccid penis prior to inflation such that the support has a snug but not tight fit on the penis. The tab 30 is shown vertically above the penis ready to be wrapped around the penis on top of the support 10. The tab 30 temporarily secures the support in the wrapped position to maintain the snug fit of the support. The desired length of the prosthesis in relation to the penis is shown in this figure. The support extends from the base of the penis to the coronal ridge of the glans. The support does not extend over the glans to leave the sensitive tissue of the glans exposed. This allows stimulation of the glans which may result in ejaculation or an erection. It is understood that the flexible property of the support ensures that the support will expand to accommodate and erection should one occur. The support will apply little constrictive force on the penis and will subsequently have little effect on the circulation of the blood within the penis.

A condom 80 is shown ready for placement on top of the prosthesis. The condom further secures the support in a tubular shape around the penis for the duration of sexual activities.

FIG. 8 shows the condom 80 disposed over the penis. The internal expandable bladder chamber of the support has been inflated to the desired circumferential size and rigidity. The condom 80 secures the prosthesis in place and provides a smooth surface for the prosthesis. It is understood theat the condom tip could be removed if desired to allow the glans of the penis to be exposed.

Once the prosthesis is positioned around the penis, adjustments to the fit of the prosthesis can easily be made. Adjustments to the rigidity and circumference can also be made from a first non-expanded condition where the bladder is non inflated and the support has little rigidity other than that provided by the stays, to a second fully expanded condition where the bladder is fully inflated and the support adds significantly to the circumference of the penis and the support has high support rigidity. These adjustments are made by the attachment of the hose 94 of ball pump 92 to the valve 90 and the subsequent insertion or removal of air from the internal expandable bladder chamber. The valve restricts air from leaking out the bladder chamber.

Following sexual activities using the prosthesis, the prosthesis may be easily cleaned for further use.

It is understood that various modifications and changes in form or detail could readily be made without departing from the spirit of the invention. Examples of such modifications include the use of fluids in the bladder of the support other than air. The length of the tab could be shorter than shown, and could possibly include an external adhesive if desired. The support could be manufactured in tube shapes of varied sizes. This would, however, deny users of the prosthesis the benefit of size adjustment. It is understood that other variations of the invention are also possible. It is therefore intended that the invention be not limited to the exact form and detail herein shown and described, nor to anything less than the whole of the invention herein disclosed and hereinafter claimed.

What is claimed is:

1. An external penile prosthesis comprising:
   a support including an expandible bladder having at least first and second elastic layers; wherein the first and second layers are secured together to include an interior expandible bladder chamber between the first and second layers;
   means to secure the support into a tube shape with the first layer providing an inside surface of the tube and the second layer providing an outside surface of the tube; wherein the support may be secured in a tube shape of predetermined size having an inside diameter, an outside diameter, and first and second ends defining a length; wherein the length is substantially equal to the length of a male penis from the base to the coronal ridge of the glans; such that the second end of the support does not extend over the glans; and wherein the tube is selectively dimensioned for a snug but not tight fit on the penis which does not cause restriction of blood flow through the veins beneath the skin of the penis;
   means for insertion of a fluid into the expandible bladder chamber;
   wherein the internal expandible bladder chamber of the support may be selectively filled with fluid from a first non-expanded condition where the support has little rigidity, to a second fully expanded condition where the support has high supportive rigidity;
   means to minimize localized constrictive forces applied to the penis resulting from the constriction of the inside diameter as the expandible bladder expands; wherein upon insertion of a fluid into the interior expandible bladder chamber, the means to minimize localized constrictive forces applied to the penis resulting from the constriction of the inside diameter cause the outside diameter of the tube to expand a greater amount than the interior of the tube constricts; and
   and wherein localized constrictive forces applied to the penis resulting from the constriction of the tube inside diameter is minimized substantially along the entire length of the tube.

2. The external penile prosthesis of claim 1, wherein the means to minimize localized constrictive forces applied to the penis resulting from the constriction of the inside diameter as the expandible bladder expands comprises the first layer of the bladder having higher rigidity than the second layer of the bladder.

3. The external penile prosthesis of claim 1, wherein the means to minimize localized constrictive forces applied to the penis resulting from the constriction of the inside diameter as the expandible bladder expands comprises substantially rigid stays disposed on the first layer of the bladder for placement proximate to the penis; such that the rigid stays minimize the force of internal fluid pressure in the interior expandible bladder chamber from applying a localized pressure on the veins of the penis.

4. The external penile prosthesis of claim 1, wherein the means to secure the support in a tube shape comprises a condom disposed on top of the support.

5. The external penile prosthesis of claim 1, wherein the support comprises a generally planar panel having a width of predetermined size to approximate the circumference of the penis for wrapping the support around the penis; and wherein the panel includes opposite side edges which are disposed proximate to each other when the support is wrapped around the penis.

6. The external penile prosthesis of claim 5, wherein the means to secure the support in a tube shape comprises a tab of material attached to the generally planar panel for stretching across the first and second side edges to secure the side edges proximate to each other.

7. The external penile prosthesis of claim 6, wherein the tab includes a width of predetermined size to approximate the circumference of the penis for wrapping the tab around the penis after the support has been wrapped around the penis for securing the support in the tube shape.

8. The external penile prosthesis of claim 7, wherein the tab includes a length substantially equal to the length of the planar support; wherein the tab comprises a cover for the support.

9. The external penile prosthesis of claim 1, wherein the means for insertion of a fluid into the expandible bladder chamber comprises a valve.

10. An external penile prosthesis comprising:
    a support including an expandible bladder having at least first and second elastic layers; wherein the first and second layers are secured together to include an interior expandible bladder chamber between the first and second layers;
    means to secure the support into a tube shape with the first layer providing an inside surface of the tube and the second layer providing an outside surface of the tube; wherein the support may be secured in a tube shape of predetermined size having an inside diameter, an outside diameter, and first and second ends defining a length; wherein the length is substantially equal to the length of a male penis from the base to the coronal ridge of the glans; such that the second end of the support does not extend over the glans; and wherein the tube is selectively dimensioned for a snug but not tight fit on the penis which does not cause restriction of blood flow through the veins beneath the skin of the penis;
    means for insertion of a fluid into the expandible bladder chamber;
    wherein the internal expandible bladder chamber of the support may be selectively filled with fluid from a first non-expanded condition where the support has little rigidity, to a second fully expanded condition where the support has high supportive rigidity;
    means to minimize localized constrictive forces applied to the penis resulting from the constriction of the inside diameter as the expandible bladder expands; wherein upon insertion of a fluid into the interior expandible bladder chamber, the means to minimize localized constrictive forces applied to the penis resulting from the constriction of the inside diameter cause the outside diameter of the tube to expand a greater amount than the interior of the tube constricts; and
    and wherein localized constrictive forces applied to the penis resulting from the constriction of the tube inside diameter is minimized at the first end of the tube which is placed over the base of the penis.

11. The external penile prosthesis of claim 10, wherein the means to minimize localized constrictive forces applied to the penis resulting from the constriction of the inside diameter as the expandible bladder expands comprises the first layer of the bladder having higher rigidity than the second layer of the bladder.

12. The external penile prosthesis of claim 10, wherein the means to minimize localized constrictive forces applied to the penis resulting from the constriction of the inside diameter as the expandible bladder expands comprises substantially rigid stays disposed on the first layer of the bladder for placement proximate to the penis; such that the rigid stays minimize the force of internal fluid pressure in the interior expandible bladder chamber from applying a localized pressure on the veins of the penis.

13. The external penile prosthesis of claim 10, wherein the means to secure the support in a tube shape comprises a condom disposed on top of the support.

14. The external penile prosthesis of claim 10, wherein the support comprises a generally planar panel having a width of predetermined size to approximate the circumference of the penis for wrapping the support around the penis; and wherein the panel includes opposite side edges which are disposed proximate to each other when the support is wrapped around the penis.

15. The external penile prosthesis of claim 14, wherein the means to secure the support in a tube shape comprises a tab of material attached to the generally planar panel for stretching across the first and second side edges to secure the side edges proximate to each other.

16. The external penile prosthesis of claim 14, wherein the tab includes a width of predetermined size to approximate the circumference of the penis for wrapping the tab around the penis after the support has been wrapped around the penis for securing the support in the tube shape.

17. The external penile prosthesis of claim 15, wherein the tab includes a length substantially equal to the length of the planar support; wherein the tab comprises a cover for the support.

18. The external penile prosthesis of claim 10, wherein the means for insertion of a fluid into the expandible bladder chamber comprises a valve.

* * * * *